(12) United States Patent
Ozawa et al.

(10) Patent No.: US 6,746,629 B2
(45) Date of Patent: Jun. 8, 2004

(54) SQUARYLIUM COMPOUNDS, FILTERS FOR PLASMA DISPLAY PANELS EMPLOYING THEM, AND PLASMA DISPLAY PANEL DEVICES

(75) Inventors: Tetsuo Ozawa, Yokohama (JP); Tetsuo Murayama, Yokohama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 22 days.

(21) Appl. No.: 09/944,184

(22) Filed: Sep. 4, 2001

(65) Prior Publication Data

US 2002/0014819 A1 Feb. 7, 2002

Related U.S. Application Data

(63) Continuation of application No. PCT/JP00/01345, filed on Mar. 6, 2000.

(30) Foreign Application Priority Data

| Mar. 5, 1999 | (JP) | 11-057944 |
| Oct. 19, 1999 | (JP) | 11-296832 |
| Oct. 28, 1999 | (JP) | 11-306563 |

(51) Int. Cl.$^7$ .............................. F21V 9/00; F21V 9/04; G02B 5/22; C07C 39/17
(52) U.S. Cl. .................... 252/589; 252/582; 252/587; 359/885; 568/644; 568/721
(58) Field of Search ................. 252/582, 587, 252/589; 359/885; 568/644, 721

(56) References Cited

U.S. PATENT DOCUMENTS 3,824,099 A 7/1974 Champ et al. ................ 96/1.5

(List continued on next page.)

FOREIGN PATENT DOCUMENTS

| EP | 0756183 A2 | 1/1997 |
| EP | 0 855 602 A2 | 7/1998 |

(List continued on next page.)

OTHER PUBLICATIONS

Meier, H., et al, "Bathochromic or hypsochromic effects via the extension of conjugation: a study of stilbenoid squarainee", Chemical Communications, 1999, Vol, 11, p. 977–978.

(List continued on next page.)

Primary Examiner—Philip C. Tucker
(74) Attorney, Agent, or Firm—Oblon, Spivak, McClelland, Maier & Neustadt, P.C.

(57) ABSTRACT

Coloring matters and filters for plasma display panels, which can effectively screen the neon emission radiated from plasma display panels. Squarylium compounds represented by the following formula (I):

(I)

$$\text{(HO)}_m \text{—Ar—C(2+)—Ar—(OH)}_m$$
$$(R)_n \qquad (R)_n$$
with O- substituents

[in the formula (I), R is a halogen atom, an alkyl group which may have a substituent, an alkoxy group which may have a substituent, or an alkenyl group which may have a substituent, m is an integer of from 1 to 4, and n is an integer of from 0 to 4], and filters for plasma display panels, made by laminating layers containing these compounds with layers containing ultraviolet absorbers and, if necessary, providing additionally near infrared screening layers, antireflection layers and/or non-glare layers.

20 Claims, 2 Drawing Sheets

U.S. PATENT DOCUMENTS

| | | | |
|---|---|---|---|
| 4,175,956 | A | 11/1979 | Haley et al. |
| 4,353,971 | A | 10/1982 | Chang et al. |
| 4,524,218 | A | 6/1985 | Baranyi et al. .............. 564/307 |
| 5,922,246 | A | 7/1999 | Matushita et al. |
| 2002/0012182 | A1 * | 1/2002 | Ozowa ....................... 359/885 |

FOREIGN PATENT DOCUMENTS

| | | |
|---|---|---|
| EP | 3 824 099 | 7/1998 |
| JP | 10-186127 | 7/1998 |
| JP | 10-204304 | 8/1998 |
| JP | 2000-43175 | 2/2000 |
| JP | 2000-345059 | 12/2000 |

OTHER PUBLICATIONS

Meier, H. et al, "Extension of the squaraine chromophore in symmetrical bis (stilbenyl) squaraines", *J. Org. Chem.*, 1997, vol. 62, No. 14. P. 4821–4826.

Rahaiah, D., et al, "Halogenated squaraine dyes as potential photochemotherapeutic agents. Synthesis and study of photophysical properties and quantum efficiencies of singlet oxygen generation", *Photochem. Photobiol.*, 1997, vol. 65, p. 783–790.

Meier, H., et al, "Bis (stilbenyl) squaraines—novel pigments with extended conjugation", *Tetrahedron Lett.*, 1996, vol. 37, No. 8, p. 1191–1194.

Angew. Chem., vol. 77, No. 15, pp. 680–681 (With English translation), No date.

H.–E. Sprenger, et al., Angew. Chem. Internat. Edit., vol. 7, No. 7, pp. 530–535, "Cylcobutenediyliym Dyes", 1968.

Dipaola–Baranyi, G. et al, "Near–infrared electrophotographic photoreceptor incorporating a hydroxy squaraine", J. Imaging Sci., 1988, Vol, 32, No. 2, p. 60–64.

* cited by examiner

SQUARYLIUM COMPOUNDS, FILTERS FOR PLASMA DISPLAY PANELS EMPLOYING THEM, AND PLASMA DISPLAY PANEL DEVICES

TECHNICAL FIELD

The present invention relates to squarylium compounds, and filters for plasma display panels employing them. Particularly, it relates to filters for plasma display panels, which are characterized by having a layer containing a specific squarylium compound and which are capable of effectively screening neon emission radiated from plasma display panels.

BACKGROUND ART

In recent years, plasma display panels have been used as display panels of various electronic appliances including large size wall-hung TVs, and their demands have increased, and it is expected that their number will continuously increase in future.

In a plasma display, a gas mixture of xenon and neon is excited by electric discharge to radiate vacuum ultraviolet rays, and emission of three primary colors is obtained by utilizing emission of red, blue and green by the respective phosphors under excitation with the vacuum ultraviolet rays. At that time, so-called neon orange light having a center wavelength of about 600 nm will be emitted when neon atoms once excited, will return to the ground state (Journal of Institute of Image Information and Television Engineers, Vol. 51, NO. 4, P.459–463 (1997)). Therefore, the plasma display has a drawback that an orange color will be mixed to a red color, whereby a bright red color is hardly obtainable.

For example, JP-A-10-204304 discloses squarylium compounds which have only OH groups as substituents on the benzene rings. However, these compound have absorption at a wavelength departing from the wavelength region of the neon orange light, and they were inadequate to screen the neon orange light.

It is an object of the present invention to provide a filter for a plasma display panel, which is capable of effectively screening neon emission. Particularly, it is intended to provide a filter for a plasma display panel excellent in light resistance.

DISCLOSURE OF THE INVENTION

The present inventors have conducted various studies and have found that the above objects can be accomplished by using a compound containing a specific squarylium compound having hydroxyl groups.

Namely, the first gist of the present invention resides in a squarylium compound represented by the following formula (I), and a filter for a plasma display panel, characterized by having a layer containing such a compound, on a transparent substrate.

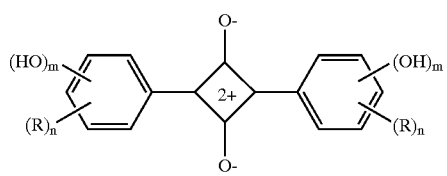

(I)

[in the formula (I), R is a halogen atom, an alkyl group which may have a substituent, an alkoxy group which may have a substituent, or an alkenyl group which may have a substituent, m is an integer of from 1 to 4, and n is an integer of from 1 to 4.]

The squarylium compound represented by the above formula (I) is characterized in that it has OH groups together with other specific substituents on the benzene rings, whereby, as compared with a compound having only OH groups as substituents on the benzene rings, the absorption maximum is shifted towards the long wavelength side, and it has the absorption maximum in the vicinity of 600 nm (particularly from 580 to 600 nm) which is the wavelength of the neon emission, whereby the neon emission can effectively be screened, and it is possible to obtain an excellent filter for a plasma display panel.

Further, the present inventors have conducted various studies and have found it possible to substantially improve the light resistance of a filter for a plasma display panel by laminating an ultraviolet absorbing layer with a layer containing a specific squarylium compound having hydroxyl groups.

Namely, the second gist of the present invention resides in a filter for a plasma display panel, characterized in that a layer containing an ultraviolet absorber is further laminated on a layer containing a squarylium compound represented by the following formula

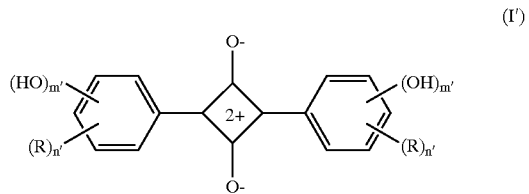

(I')

[in the formula (I'), R is a halogen atom, an alkyl group which may have a substituent, an alkoxy group which may have a substituent, or an alkenyl group which may have a substituent, m' is an integer of from 1 to 4, and n' is an integer of from 0 to 4.]

Further, the present inventors have found it possible to obtain a filter for a plasma display panel, having a better performance, by further providing a near infrared screening layer, an electromagnetic wave screening layer, an antireflection layer or a glare-preventing (non-glare) layer, in addition to the layer containing a squarylium compound, in the filter for a plasma display panel thus obtained.

Further, still another gist of the present invention relates to a plasma display panel device having such a filter for a plasma display panel on a screen of a plasma display panel.

BEST MODE FOR CARRYING OUT THE INVENTION

Figure 1:
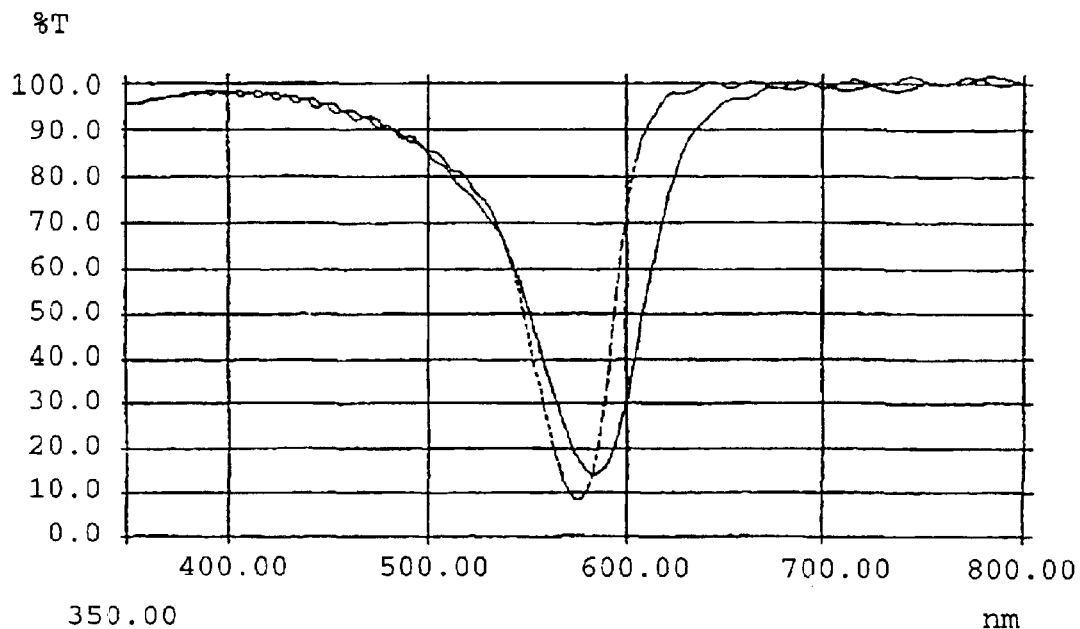
FIG. 1 shows transmittance curves of the coating films obtained in Example 1-1 (solid line) and COMPARATIVE EXAMPLE 1-1 (dotted line).

Now, the present invention will be described in detail. The squarylium compound as the first gist of the present invention is represented by the above formula (I).

Preferred examples of substituent R in the formula (I) may be the following (i) to (vii).

(i) A halogen atom such as a fluorine atom, a chlorine atom or a bromine atom;

(ii) a $C_{1-20}$ linear or branched alkyl group such as a methyl group, an ethyl group, a propyl group, a butyl group, a pentyl group, a hexyl group, a heptyl group, an octyl group, a decyl group, an undecyl group, a dodecyl group, a tridecyl group or a pentadecyl group;

(iii) the above-mentioned $C_{1-20}$ linear or branched alkyl group having as a substituent, a hydroxyl group, an alkoxycarbonyl group such as a methoxycarbonyl group, an ethoxycarbonyl group or a butoxycarbonyl group, an acyloxycarbonyl group such as an acetyloxycarbonyl group or a propionylcarbonyl group, an alkoxy-carbonyloxy group such as a methoxycarbonyloxy group, an ethoxycarbonyloxy group or a butoxycarbonyloxy group, a cyclohexyl group, a phenyl group or the like;

(iv) a $C_{1-20}$ linear or branched alkoxy group such as a methoxy group, an ethoxy group, a propoxy group, a butoxy group, a pentyloxy group, a hexyloxy group, a heptyloxy group, an octyloxy group, a decyloxy group, an undecyloxy group, a dodecyloxy group, a tridecyloxy group, or a pentadecyloxy group;

(v) the above-mentioned $C_{1-20}$ linear or branched alkoxy group having as a substituent, a $C_{1-8}$ alkoxy group such as a methoxy group, an ethoxy group, a propoxy group, a butoxy group, a pentyloxy group, a hexyloxy group, a heptyloxy group, or an octyloxy group;

(vi) an alkenyl group such as an ethenyl group;

(vii) an alkenyl group such as an ethenyl group, which is substituted by, as a substituent, an alkyl group such as a methyl group, an ethyl group, a propyl group, a butyl group, a pentyl group, a hexyl group, a heptyl group, an octyl group or a decyl group, a phenyl group, a 4-hydroxyphenyl group, a 4-alkoxy (such as a $C_{1-10}$ alkoxy group) phenyl group, a 3,4-bisalkoxy (such as a $C_{1-10}$ alkoxy group) phenyl group, a 3,5-bisalkoxy (such as a $C_{1-10}$ alkoxy group) phenyl group, or a 3,4,5-trisalkoxy (such as a $C_{1-10}$ alkoxy group) phenyl group.

Among them, R is particularly preferably a $C_{1-6}$ linear or branched alkyl group; a $C_{1-6}$ linear or branched alkyl group substituted by a hydroxyl group or an alkoxy-carbonyl group; a $C_{1-6}$ alkoxy group; or an ethenyl group having a substituent.

Further, when m=3, the compound has no minimum value in transmittance in the vicinity of from 400 to 500 nm, whereby the transmittance of from 400 to 500 nm is good, and the yield, purity, etc. in the synthesis are good, such being more preferred. Most preferred is a case wherein m=3, and n=1, and particularly R is an alkyl group which may have a substituent. Further, among such squarylium compounds, symmetrical squarylium compounds are preferred, since their production is easy.

The squarylium compound of the formula (I) can be produced by e.g. the method disclosed in Angew.Chem. 77, 680–681 (1965) or a method similar thereto.

Namely, it can be synthesized by subjecting 2 mols of a phenol compound represented by the following formula (II):

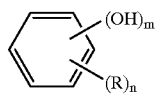
(II)

[in the formula, R, m and n are as defined in the above formula (I)] and 1 mol of squalic acid to dehydration condensation under heating at a temperature of from 70 to 150° C. in ethanol, acetic acid, a n-butyl alcohol/toluene mixed solvent or a n-butyl alcohol/benzene mixed solvent.

Typical examples of the formula (I) will be shown below.

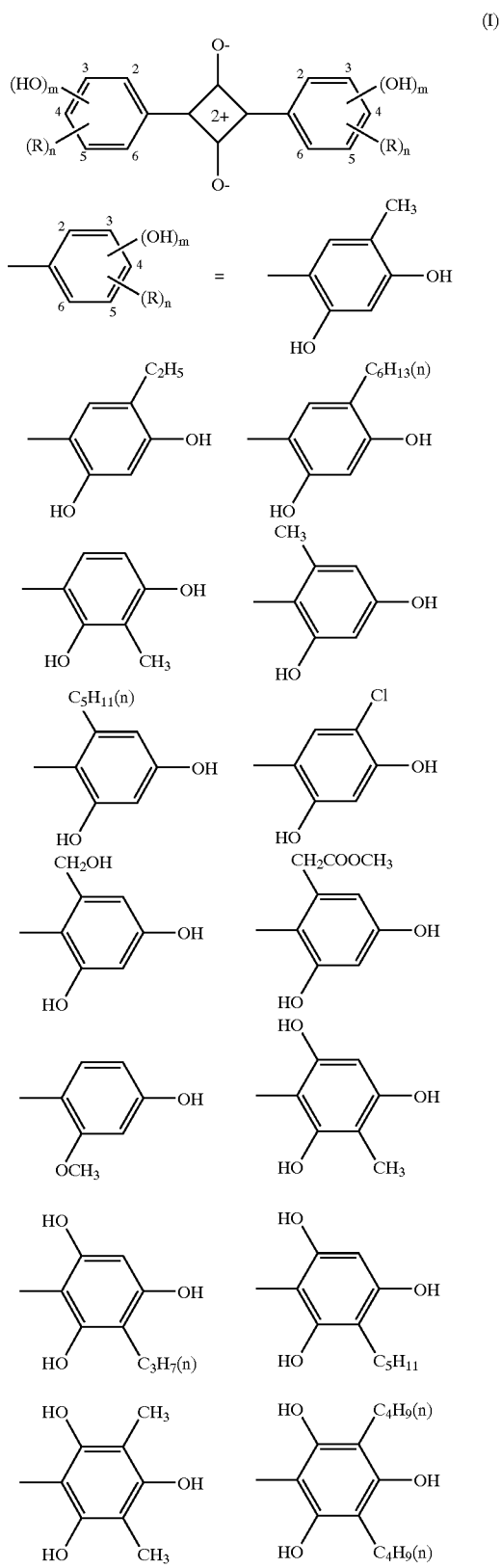

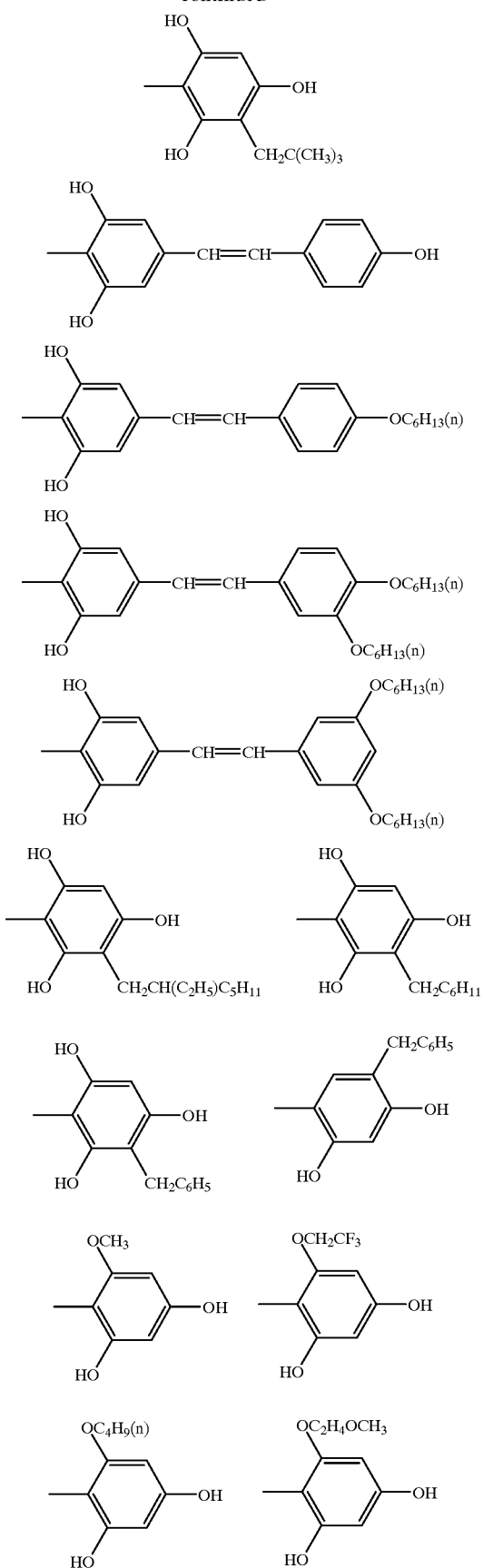

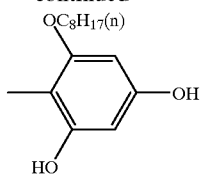

A coating fluid containing the squarylium compound of the above formula (I) is coated on a transparent substrate formed into a film or sheet, whereby a layer containing the squarylium compound, can be obtained. By using such a layer containing the squarylium compound, an excellent filter for a plasma display panel can be obtained.

On the other hand, for the second gist of the present invention i.e. for the filter for a plasma display panel, wherein a layer containing an ultraviolet absorber is further laminated on a layer containing the squarylium compound on the transparent substrate, a specific squarylium compound represented by the following formula (I') is employed:

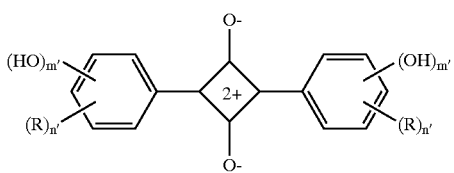

(I')

[in the formula (I'), R is a halogen atom, an alkyl group which may have a substituent, an alkoxy group which may have a substituent, or an alkenyl group which may have a substituent, m' is an integer of from 1 to 4, and n' is an integer of from 0 to 4.]

As the squarylium compound represented by the formula (I'), one type may be employed, but two or more types of such compound may be selected for use.

As the squarylium compound represented by the formula (I'), in addition to the compound represented by the above-mentioned formula (I) (i.e. wherein n'=1 to 4), a compound having only hydroxyl groups as substituents on the benzene rings constituting the squarylium compound (i.e. wherein n'=0) may also be employed. As typical examples of such a compound having only hydroxyl groups as substituents on the benzene rings, the following compounds may be mentioned, as represented by the constituting component having a benzene ring constituting the formula (I'), and particularly preferred are those wherein m'=2 or 3, especially preferably m'=3, since their production is easy.

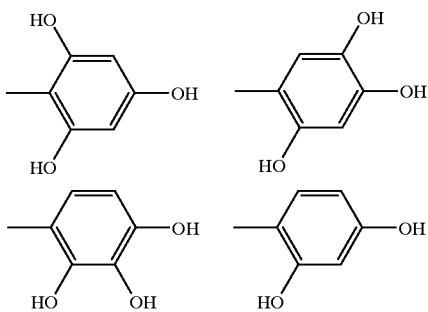

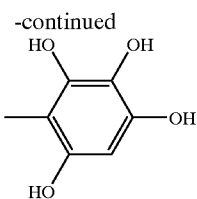

Such squarylium compounds can be synthesized in the same manner as the above-mentioned squarylium compounds represented by the formula (I).

The following compounds may be mentioned as preferred specific examples of the formulae (I) and (I').

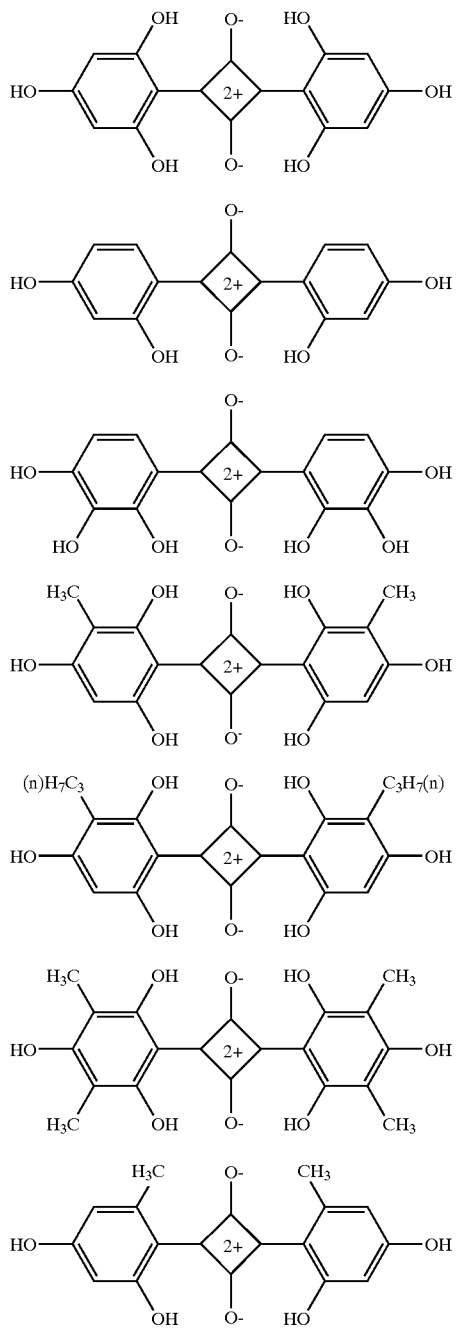

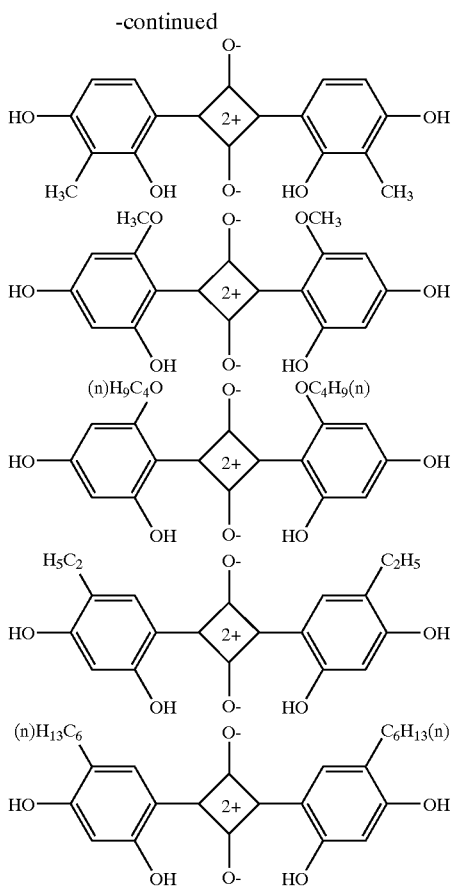

Further, when the squarylium compound represented by the above (I') is used for the preparation of a filter for a plasma display panel, with the compound having only hydroxyl groups as substituents on the benzene rings, the position of the absorption maximum may sometimes be slightly shifted towards the short wavelength side from 580 to 590 nm which is the neon emission wavelength. In such a case, a suitable colorant may be incorporated to obtain a filter for a plasma display panel capable of effectively screening neon emission. To obtain a film for a plasma display panel employing the squarylium compound of the present invention, a coating fluid containing the squarylium compound may be coated on a transparent substrate formed into a film or sheet.

The coating fluid may be prepared by a method wherein the squarylium compound is dissolved in an organic solvent together with a binder, or a method wherein the squarylium compound pulverized to a particle size of from 0.1 to 3 μm is dispersed in a solvent together with a binder, if necessary by using a dispersant. Here, the content of the squarylium compound, the binder, the dispersant, etc. to be dissolved or dispersed in the solvent, is from 0.5 to 50 wt %, based on the coating fluid, and the proportion of the squarylium compound in the squarylium compound, the binder and the dispersant, is from 0.05 to 50 wt %, preferably from 0.1 to 20 wt %.

As the dispersant to be used as the case requires, a polyvinyl butyral resin, a phenoxy resin, a rosin-modified phenol resin, a petroleum resin, a hardened rosin, a rosin ester, a maleic rosin or a polyurethane resin, may, for example, be mentioned. Its amount is from 0.5 to 150 times by weight, preferably from 10 to 100 times by weight, relative to the squarylium compound.

As the binder to be used, an acrylate resin such as a polymethyl methacrylate resin, a polyethyl acrylate resin, a polycarbonate resin, an ethylene/vinyl alcohol copolymer resin, an ethylene/vinyl acetate copolymer resin, an AS resin, a polyester resin, a vinyl acetate resin, a polyvinyl butyral resin, PVPA, a polystyrene resin, a phenol resin, a phenoxy resin, polysulfone, nylon, a cellulose resin, or a cellulose acetate resin, may, for example, be mentioned. Its amount is from 10 to 500 times by weight, preferably from 50 to 350 times by weight, relative to the squarylium compound.

The wavelength at the minimum value in the transmittance curve of the layer containing the squarylium compound of the present invention shows a different value depending upon the binder to be used. Accordingly, in order to effectively screening neon emission in the vicinity of 600 nm (particularly from 580 to 600 nm), it is advisable to select the binder resin depending upon the type of the squarylium compound.

At that time, it is advisable to select the combination of the squarylium compound and the binder resin, so that neon emission in the vicinity of 600 nm is effectively screened, without screening green color emission in the vicinity of from 500 to 530 nm and red color emission with a wavelength longer than 600 nm, as the emission colors of the phosphors. For this purpose, the transmittance curve of the squarylium compound preferably has a sharp valley shape, and the wavelength at the minimum value in the transmittance curve of the squarylium compound is preferably from 570 nm to 605 nm, particularly preferably from 580 to 600 nm. For the purpose of suppressing neon emission, the minimum value in the transmittance curve is preferably at most 20%, more preferably at most 15%. As it is desired to have a sharp valley shape, the width at the 50% transmittance is preferably not more than 60 nm, when the minimum transmittance is 10%. Further, to secure brightness of the visual field, the squarylium compound preferably has no local minimum value in the transmittance curve other than the minimum value in the vicinity of 600 nm in the transmittance curve, or even if it has such a local minimum value, the value is preferably at least 70%, more preferably at least 80%, and the visual light transmittance is preferably at least 40%, more preferably at least 50%.

Further, the light resistance of the squarylium compound of the present invention varies depending upon the binder resin. When a polyester resin is employed among binder resins, the light resistance of the squarylium compound is better.

Further, the colorant of the present invention has absorption in a region ranging from a purple color to a blue color. Accordingly, the filter of the present invention can be used also as a filter for adjusting the color temperature.

A coating fluid containing the squarylium compound may be coated by a known coating method such as a dipping method, a flow coating method, a spraying method, a bar coating method, a gravure coating method, a roll coating method, a blade coating method or an air knife coating method. The coating is carried out so that the film thickness will be from 0.1 to 30 μm, preferably from 0.5 to 10 μm.

The material for a transparent substrate constituting the filter for a plasma display panel of the present invention, is not particularly limited, so long as it is a material which is substantially transparent and which shows no substantial absorption or scattering. Specific examples may be glass, a polyolefin resin, an amorphous polyolefin resin, a polyester resin, a polycarbonate resin, a poly(meth)acrylate resin, a polystyrene, a polyvinyl chloride, a polyvinyl acetate, a polyallylate resin, and a polyether sulfone resin.

Among them, an amorphous polyolefin resin, a polyester resin, a polycarbonate resin, a poly(meth)acrylate resin, a polyallylate resin or a polyether sulfone resin, may, for example, be particularly preferred.

To such a resin, commonly known additives, such as an antioxidant of phenol type or phosphorus type, a flame retardant of halogen type or phosphoric acid type, an anti-thermal aging agent, an ultraviolet absorber, a lubricant and an antistatic agent, may be incorporated.

Further, the above resin is formed into a film or sheet (plate) by a known method such as injection molding, T-die molding, calender molding or compression molding, or by a method wherein it is dissolved in an organic solvent, followed by casting. The thickness is preferably within a range of from 10 μm to 5 mm depending upon the purpose. The base material constituting such a transparent substrate may be non-stretched or stretched. Further, it may be laminated with other base material.

Further, the transparent substrate may be subjected to surface treatment by a conventional method such as corona discharge treatment, flame treatment, plasma treatment, glow discharge treatment, surface roughening treatment or chemical treatment, or coating with e.g. an anchor coating agent or a primer.

The filter for a plasma display panel of the present invention may be produced also by directly dissolving or dispersing the squarylium compound in various resins constituting the transparent substrate or in other resins, molding or filming the obtained resin containing the squarylium compound by a molding technique such as injecting molding, T-die molding, calender molding or compression molding, and bonding the product with other transparent substrate, as the case requires.

Further, instead of the above coating method of the coating fluid, the squarylium compound may be dyed to a resin sheet or film constituting the transparent substrate or to other resin sheet (plate) or film, and bonding it with other transparent substrate, as the case requires.

Further, in order to increase the light resistance of the filter containing the squarylium compound of the formula (I) of the present invention, an ultraviolet absorber may be incorporated in the squarylium compound-containing layer, or a transparent resin layer containing an ultraviolet absorber, may be laminated on the outer side. As the resin to be used for the transparent resin layer, the resin mentioned above as a binder for the squarylium compound, may be used.

In such a case, the effect for improvement of the light resistance of the squarylium compound is better by a method of laminating an ultraviolet absorbing layer rather than the method of incorporating an ultraviolet absorber in the same layer as the squarylium compound as disclosed in JP-A-10-204304. The lamination method may be such that lamination is made in contact with the layer containing the squarylium compound, or lamination may be made on a transparent substrate coated with a layer containing the squarylium compound on the side opposite to the layer containing the squarylium compound.

On the other hand, in the case of a compound wherein n'=0 (i.e. one having only hydroxyl groups as substituents on the benzene rings constituting the squarylium compound) among the squarylium compounds represented by the formula (I') of the present invention, the layer containing the squarylium compound and an ultraviolet absorbing layer are laminated for use necessarily as separate layers, because in the case where the substituents on the benzene rings are only hydroxyl groups, if the ultraviolet absorber is present in combination, there will be such an inconvenience that the light resistance of the squarylium compound will be substantially impaired.

When a layer containing an ultraviolet absorber is provided as a separate layer, lamination is conducted so that the thickness of the ultraviolet absorbing layer will be from 0.1 to 30 µm, preferably from 0.5 to 10 µm. Such an ultraviolet absorbing layer may be a layer containing an ultraviolet absorber to screen ultraviolet rays, or a layer which is capable of effectively screening ultraviolet rays even without employing an ultraviolet absorber, for example, a layer capable of screening at least 20% of the wavelength at 380 mm, preferably a layer capable of screening at least 40%. Further, instead of forming the ultraviolet absorber-containing layer by coating, a commercially available ultraviolet screening filter may be laminated for use. As such a filter, Sharp Cut Filter SC-38, SC-39 or SC-40 (manufactured by Fuji Photo Film Co., Ltd.) may, for example, be mentioned.

As the ultraviolet absorber, an organic ultraviolet absorber or an inorganic ultraviolet absorber may be used. The organic ultraviolet absorber may, for example, be a benzotriazole compound such as 2-(2'-hydroxy-5'-t-butylphenyl) benzotriazole or 2-(2'-hydroxy-3',5'-di-t-butylphenyl) benzotriazole, a benzophenone compound such as 2-hydroxy-4-methoxybenzophenone or 2-hydroxy-4-n-octyloxy benzophenone, or a hydroxybenzoate compound such as phenyl salicylate, 4-t-butylphenyl salicylate, n-hexadecyl 2,5-t-butyl-4-hydroxybenzoate or 2,4-di-t-butylphenyl 3',5'-di-t-butyl-4'-hydroxybenzoate. The inorganic ultraviolet absorber may, for example, be titanium oxide, zinc oxide, cerium oxide, iron oxide or barium sulfate. As the ultraviolet absorber, the wavelength at a 50% transmittance is preferably from 350 to 420 nm, more preferably from 360 nm to 400 nm. If the wavelength is less than 350 nm, the ultraviolet shielding performance tends to be low, and it the wavelength is more than 420 nm, coloration tends to be intensive, such being undesirable.

The filter for a plasma display panel of the present invention may be provided with a near infrared screening layer or an electromagnetic wave screening layer, or it may be provided with an antireflection layer to prevent reflection of an exterior light such as fluorescent lamp to the surface, or with a glare-preventing (non-glare) layer. These layers are laminated so that the thickness of each layer will be from 0.1 to 30 µm, preferably from 0.5 to 10 µm.

The near infrared screening layer is provided on the front side of the display for the purpose of preventing malfunction in the transmission type optical communication or remote control, due to near infrared rays radiated from the plasma display. The screening range of near infrared rays is from 800 to 1000 nm for the remote control or the transmission type optical communication, as a particularly problematic wavelength, and a near infrared absorbing material having absorption in the range, is used. As such a near infrared absorbing material, a near infrared absorbing dye such as a nitroso compound and its metal complex, a cyanine compound, a dithiol nickel complex compound, an aminothiol nickel complex compound, a phthalocyanine compound, a triallyl methane compound, an imonium compound, a diimonium compound, a naphthoquinone compound, an anthraquinone compound, an amino compound or an aminium salt compound, or a near infrared absorbing compound such as carbon black, indium tin oxide or antimony tin oxide, may be used alone or in combination.

The electromagnetic wave screening layer may be formed by vapor deposition or sputtering of e.g. a metal oxide. Usually, indium tin oxide (ITO) is common, but a dielectric layer and a metal layer may alternately be laminated on a substrate by e.g. sputtering, whereby light of 1000 nm or more, can be screened. As a dielectric layer, a transparent metal oxide such as indium oxide or zinc oxide may be mentioned, and as a metal layer, silver or a silver/palladium alloy is common, and usually, starting from a dielectric layer, three layers, five layers, seven layers or about 11 layers are laminated. As the substrate, the filter may be used as it is, or vapor deposition or sputtering is carried out on a resin film or glass, followed by bonding to the filter.

The antireflection layer may be formed by a method of laminating an inorganic substance such as a metal oxide, a fluoride, a silicide, a boride, a carbide, a nitride, or a sulfide in a single layer or multilayers by e.g. a vacuum vapor deposition method, a sputtering method, an ion plating method or an ion beam assist method, or a method of laminating resins having different refractive indices, such as an acryl resin and a fluorine resin, in a single layer or multilayers, in order to suppress the reflection on the surface, thereby to improve the transmittance of the filter. Otherwise, a film having antireflection treatment applied, may be bonded on the filter.

Further, a glare-preventing layer (non-glare layer) may also be provided. The non-glare layer may be formed by a method wherein a fine powder of e.g. silica, melamine or acryl, is formed into an ink and coated on the surface, to let the transmitted light scatter for the purpose of widening the visual angle of the filter. Curing of the ink may be carried out by thermal curing or photo curing. Further, the non-glare treated film may be bonded on the filter. Further, a hard coat layer may be provided, if necessary.

To the filter for plasma display of the present invention, an adhesive layer may be provided as the outermost layer. By this adhesive layer, this filter is bonded on the front side of plasma display during the production process of a plasma display, or after the production of the plasma display, whereby it is possible to obtain a plasma display panel device which is capable of efficiently screening neon emission and which is excellent also in light resistance.

By the above construction, it will be unnecessary to sequentially provide a near infrared absorbing layer, an electromagnetic wave shielding layer and other layer on the front side of the plasma display itself, and further, the filter will be integrated with the plasma display, whereby it is possible to make the plasma display to be thin.

As the adhesive to constitute the adhesive layer, a rubber such as styrene/butadiene rubber, polyisoprene, natural rubber, neoprene or butyl rubber, or a low polymerization degree polymer of e.g. a polyalkyl acrylate such as a polymethyl acrylate, a polyethyl acrylate or a polybutyl acrylate, may be used alone or in combination with a tackifier such as piccolite, polybel or rosin ester.

If bubbles enter between the filter and the surface of the plasma display when the filter is bonded to the plasma display, there will be a serious practical problem such that the image tends to distort or tends to be hardly seen. Accordingly, it is necessary to pay an adequate attention to such inclusion of bubbles.

Further, the temperature of the surface of the plasma display itself becomes very high, and accordingly, it should be avoided to use an adhesive which generates a gas under heating.

In a case where generation of a gas is likely, addition of e.g. an absorber should better be considered. For such reasons, it is preferred to employ an adhesive to provide a 180° peel strength of at least 300 g/cm, preferably at least 400 g/cm after bonding a polyester film of 30 μm to a glass sheet of 3 mm and holding them at 80° C. for ten days.

Specifically, one prepared by dispersing or dissolving a polymer type adhesive such as a polyalkyl acrylate or a rubber type adhesive such as styrene/butadiene rubber or natural rubber in a solvent system comprising an organic solvent of e.g. halogen type, alcohol type, ketone type, ester type, ether type, aliphatic hydrocarbon type or aromatic hydrocarbon type, alone or in combination of a plurality of such organic solvents, and adjusting the viscosity, was coated by a coating method such as a dipping method, a flow coating method, a spraying method, a bar coating method, a gravure coating method, a roll coating method, a blade coating method or an air knife coating method, followed by drying the solvent to form an adhesive layer.

The thickness of the adhesive layer at that time, is usually from 5 to 100 μm, preferably from 10 to 50 μm. It is also advisable to protect the adhesive layer until it is bonded to the surface of a plasma display, by providing a release film on the surface of the adhesive layer so that dusts, etc. will not deposit on the adhesive layer.

In such a case, it is advisable to form a non-adhesive portion by forming a portion where no adhesive layer is provided or by sandwiching a non-adhesive film, between the release film and the adhesive layer, along the peripheral portion of the filter, thereby to provide a release-initiating portion, whereby the operation at the time of bonding will be easy.

Further, this filter for a plasma display panel can be used alone or in the form of a laminate having a transparent glass or other transparent resin plate or the like bonded thereto. When the filter for a plasma display panel of this application is used to obtain a plasma display panel device, it can be used without any particular limitation, so long as the plasma display panel device is a known display device or a commercially available product.

Such a plasma display panel device is a device to carry out display of a color image by the following principle. Between a front glass sheet and a rear glass sheet, display electrodes and cells corresponding to respective pixels (R (red), G (green), B (blue)) provided between the pair of glass sheets, are provided, and xenon gas or neon gas is sealed in the cells. On the other hand, on the rear glass sheet side in the cells, phosphors corresponding to the respective pixels are coated. By discharge between the display electrodes, the xenon gas or neon gas in the cells will be excited to emit ultraviolet rays. And, the phosphors are eradiated by the ultraviolet rays to generate visible lights corresponding to the respective pixels. And, address electrodes are provided to the rear glass sheet, and display of a color image is carried out by controlling which discharge cells should be displayed by applying signals to the address electrodes.

Now, practical embodiments of the present invention will be described with reference to Examples. However, it should be understood that the present invention is by no means restricted to such Examples.

EXAMPLE 1-1

Preparation of a squarylium compound of the formula (I) wherein R=methyl group, n=1 (substituted position: 3-position) and m=3 (substituted positions: 2, 4 and 6-positions)

0.45 g of 2,4,6-trihydroxytoluene, 0.18 g of 3,4-dihydroxy-3-cyclobutene-1,2-dione and 15 ml of acetic acid were added to a reactor and refluxed for 4 hours under heating. After completion of the reaction, the reaction mixture was cooled, and the precipitates were collected by filtration, washed with a 1:1 mixed solvent of methanol and water and dried to obtain 0.32 g of the desired compound.

Visible region absorption λ max: 576 nm (tetrahydrofuran)

Mass spectrum MALDI method (NEGA): m/z=357 (M-H)

EXAMPLE 1-2

Preparation of a squarylium compound of the formula (I) wherein R=n-propyl, n=1 (substituted position: 3-position) and m=3 (substituted positions: 2, 4 and 6-positions)

Treatment was carried out in the same manner as in Example 1-1 except that instead of 0.45 g of 2,4,6-trihydroxytoluene, an equimolar amount of 1-n-propyl-2,4,6-trihydroxybenzene was used, to obtain 0.32 g of the desired compound.

Visible region absorption λ max: 577 nm (tetrahydrofuran)

Mass spectrum MALDI method (NEGA): m/z=413 (M-H)

EXAMPLE 1-3

Preparation of a squarylium compound of the formula (I) wherein R=methyl group, n=1 (substituted position: 3-position) and m=2 (substituted positions: 2 and 4-positions)

Instead of 0.45 g of 2,4,6-trihydroxytoluene used in Example 1-1, an equimolar amount of 2-methylresorcinol was used, and instead of 15 ml of acetic acid, a mixed solvent comprising 20 cc of n-butanol and 20 cc of toluene, was used, and they were added to a reactor equipped with a jean stark apparatus and refluxed for 4 hours under heating. After completion of the reaction, the reaction mixture was cooled, and the precipitates were collected by filtration and purified by column chromatography using silica gel and using chloroform as a separating solvent, followed by drying to obtain 0.17 g of the desired compound.

Visible region absorption λ max: 575 nm (cyclohexanone)

Mass spectrum MALDI method (NEGA): m/z=325 (M-H)

EXAMPLE 1-4

Preparation of a squarylium compound of the formula (I) wherein R=ethyl group, n=1 (substituted position: 5-position) and m=2 (substituted positions: 2 and 4-positions)

Instead of 2-methylresorcinol used in Example 1-3, an equimolar amount of 4-ethylresorcinol was used, and added to a reactor equipped with a jean stark apparatus and refluxed for 4 hours under heating. After completion of the reaction, the reaction mixture was cooled, and the precipitates were collected by filtration, washed with a 1:1 mixed solvent of methanol and water and dried to obtain 0.1 g of the desired compound.

Visible region absorption λ max: 593 nm (tetrahydrofuran)

Mass spectrum MALDI method (NEGA): m/z=353 (M-H)

EXAMPLES 1-5

1) 0.36 g of a 0.63% dimethoxyethane solution of the squarylium compound prepared in Example 1-1 and 3 g of a 20% dimethoxyethane solution of a polyester resin (Biron 200; manufactured by Toyobo Co. Ltd.) were mixed and coated by a bar coater on a polyethylene terephthalate film (PET film "T100E", manufactured by Diawheelhekist Company, thickness: 100 μm), followed by drying to obtain a coating film having a thickness of 6 μm.

The transmittance of this coating film was measured by Hitachi spectrophotometer (U-3500). The transmittance curve is shown in FIG. 1. The wavelength at the minimum value of the transmittance was 584 nm, and the transmittance was 14.5%.

Further, in this case, the wavelength width at a transmittance of 50% was 56 nm. Further, the visible light transmittance of this neon emission screening filter was 54.0%, and it was a bright filter having a high transmittance.

2) A sharp cut filter SC-39 (manufactured by Fuji Photo Film Co., Ltd.) was laminated on the polyester resin side on the side opposite to the squarylium compound-containing layer side of the coating film of the above 1), to obtain a filter for a plasma display panel having good light resistance. The wavelength at a 50% transmittance of this ultraviolet absorbing layer was 386 nm.

Using a xenon fadeometer (FAL-25AX-HC.B.EC, manufactured by Suga Test Instruments Co., Ltd.), evaluation of light resistance was carried out (80-hour exposure) as between a case where the above-mentioned ultraviolet absorbing layer of a neon emission screening filter was laminated and a case where such a layer was not laminated. The colorant-remaining ratio (%) was measured by the absorption by Hitachi spectrophotometer (U-3500), whereby it was 91.4% with the former, while it was 75.0% with the latter.

The former was exposed from the ultraviolet absorbing layer side, and the latter was exposed from the squarylium compound-containing layer side.

COMPARATIVE EXAMPLE 1-1

0.36 g of a 0.63% dimethoxyethane solution of a squarylium compound prepared of the formula (I) wherein m=3 (substituted positions: 2, 4, and 6-positions) and n=0, and 3 g of a 20% dimethoxyethane solution of a polyester resin (Biron 200; manufactured by Toyobo Co. Ltd.) were mixed and coated by a bar coater on a polyethylene terephthalate film (PET film "T100E", manufactured by Diawheelhekist Company, thickness: 100 μm), followed by drying to obtain a coating film having a thickness of 6 μm.

The transmittance of this coating film was measured by Hitachi spectrophotometer (U-3500). The transmittance curve is shown in FIG. 1. The wavelength at the minimum value of the transmittance was 576 nm, and the transmittance was 8.2%. The wavelength at the minimum value of the transmittance was apart from the wavelength region of the neon emission of from 580 to 600 nm, and it was a filter not preferable as a neon emission screening filter.

EXAMPLE 1-6

1) 0.36 g of a 0.81% dimethoxyethane solution of the squarylium compound prepared in Example 1-2 and 3 g of a 20% dimethoxyethane solution of a polyester resin (Biron 200; manufactured by Toyobo Co. Ltd.) were mixed and coated by a bar coater on a polyethylene terephthalate film (PET film "T100E", manufactured by Diawheelhekist Company, thickness: 100 μm), followed by drying to obtain a coating film having a thickness of 6 μm.

Figure 2:
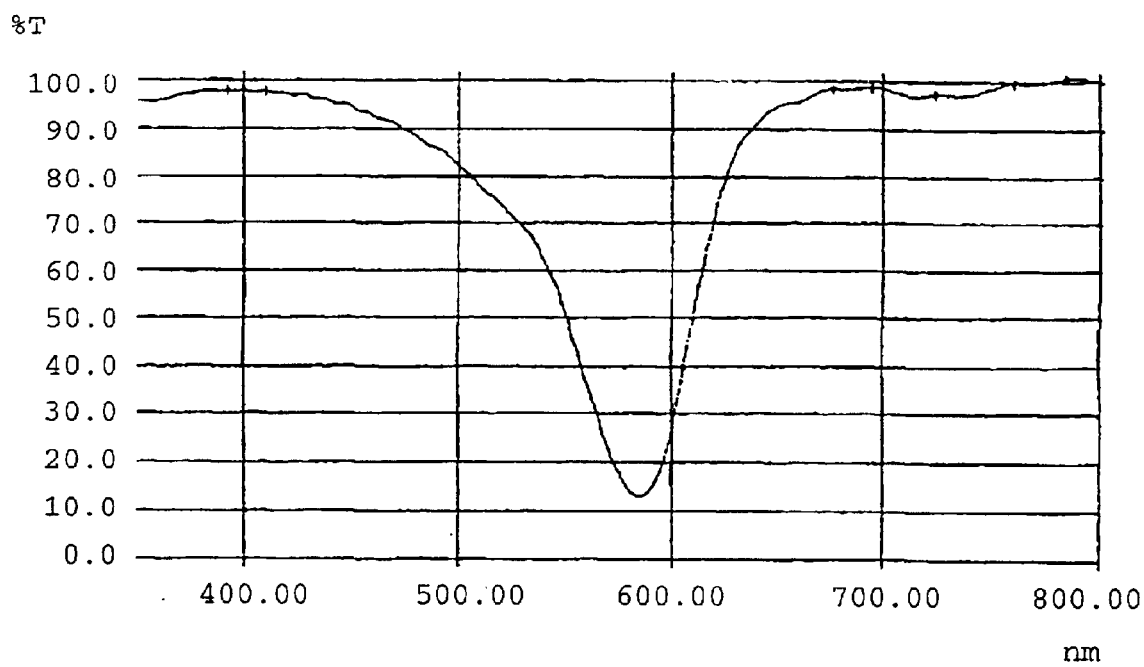
FIG. 2 shows a transmittance curve of the coating film obtained in Example 1-2.

The transmittance of this coating film was measured by Hitachi spectrophotometer (U-3500). The transmittance curve is shown in FIG. 2. The wavelength at the minimum value of the transmittance was 585 nm, and the transmittance was 13.7%.

Further, in this case, the wavelength width at a transmittance of 50% was 58 nm. Further, the visible light transmittance of this neon emission screening filter was 52.5%, and it was a bright filter having a high transmittance.

2) A sharp cut filter SC-39 (manufactured by Fuji Photo Film Co., Ltd.) was laminated on the polyester resin side on the side opposite to the squarylium compound-containing layer side of the coating film of the above 1), to obtain a filter for a plasma display panel having good light resistance. The wavelength at the 50% transmittance of this ultraviolet absorbing layer was 386 nm.

Using a xenon fadeometer (FAL-25AX-HC.B.EC, manufactured by Suga Test Instruments Co., Ltd.), evaluation of light resistance was carried out (80-hour exposure) as between a case where the above-mentioned ultraviolet absorbing layer of a neon emission screening filter was laminated and a case where such a layer was not laminated. The colorant-remaining ratio (%) was measured by the absorption by Hitachi spectrophotometer (U-3500), whereby it was 88.9% with the former, while it was 69.4% with the latter.

The former was exposed from the ultraviolet absorbing layer side, and the latter was exposed from the squarylium compound-containing layer side.

EXAMPLE 1-7

1) 0.36 g of a 0.63% dimethoxyethane solution of the squarylium compound prepared in Example 1-3 and 3 g of a 20% dimethoxyethane solution of a polyester resin (Biron 200; manufactured by Toyobo Co. Ltd.) were mixed and coated by a bar coater on a polyethylene terephthalate film (PET film "T100E", manufactured by Diawheelhekist Company, thickness: 100 μm), followed by drying to obtain a coating film having a thickness of 6 μm.

The transmittance of this coating film was measured by Hitachi spectrophotometer (U-3500). The wavelength at the minimum value of the transmittance was 584 nm, and the transmittance was 16.4%.

Further, in this case, the wavelength width at a transmittance of 50% was 41 nm. Further, the visible light transmittance of this neon emission screening filter was 59%, and it was a bright filter having a high transmittance.

2) An ultraviolet absorbing coating fluid comprising an isocyanate resin as a binder and zinc oxide as an ultraviolet absorber (ZR-133 (49 wt % of a curing agent was added), manufactured by Sumitomo Osaka Cement Co., Ltd.) was coated by a bar coater on the polyethylene terephthalate resin side on the side opposite to the squarylium compound-containing layer side of the coating film of the above 1), followed by drying to form an ultraviolet absorbing layer having a thickness of 3 μm, thereby to obtain a filter for a plasma display panel having good light resistance. The wavelength at the 50% transmittance of this ultraviolet absorbing layer was 383 nm.

Using a xenon fadeometer, evaluation of light resistance was carried out (40-hour exposure) as between a case where the above-mentioned ultraviolet absorbing layer of the neon emission screening filter was laminated and a case where such a layer was not laminated. The colorant-remaining ratio (%) was measured by the absorption by Hitachi spectrophotometer (U-3500), whereby it was 97.5% with the former, while it was 82.1% with the latter.

The former was exposed from the ultraviolet absorbing layer side, and the latter was exposed from the squarylium compound-containing layer side.

EXAMPLE 1-8

1) 0.36 g of a 0.63% dimethoxyethane solution of the squarylium compound prepared in Example 1-4 and 3 g of a 20% dimethoxyethane solution of a polyethylene terephthalate resin (Biron 200; manufactured by Toyobo Co. Ltd.) were mixed and coated by a bar coater on a polyethylene terephthalate film (PET film "T100E", manufactured by Diawheelhekist Company, thickness: 100 μm), followed by drying to obtain a coating film having a thickness of 6 μm.

The transmittance of this coating film was measured by Hitachi spectrophotometer (U-3500). The wavelength at the minimum value of the transmittance was 599 nm, and the transmittance was 6.26%.

Further, in this case, the wavelength width at a transmittance of 50% was 58 nm. Further, the visible light transmittance of this neon emission screening filter was 57%, and it was a bright filter having a high transmittance.

2) By the same treatment as in Example 1, a zinc oxide-containing ultraviolet absorbing layer having a thickness of 3 μm was formed on the polyethylene terephthalate resin side on the side opposite to the squarylium compound-containing layer side of the coating film of the above 1) to obtain a film for a plasma display panel having good light resistance. The wavelength at the 50% transmittance of this ultraviolet absorbing layer was 383 nm.

Using a xenon fadeometer, evaluation of light resistance was carried out (40-hour exposure) as between a case where the above-mentioned ultraviolet absorbing layer of the neon emission screening filter was laminated and a case where such a layer was not laminated. The colorant-remaining ratio (%) was measured by the absorption by Hitachi spectrophotometer (U-3500), whereby it was 87.0% with the former, while it was 61.0% with the latter.

The former was exposed from the ultraviolet absorbing layer side, and the latter was exposed from the squarylium compound-containing layer side.

EXAMPLE 1-9

Example for Forming a Near Infrared Screening Layer 0.36 g of a 0.63% of a diimonium type near infrared absorbing dye (a hexafluoro antimonate of N,N,N',N'-tetrakis(p-dibutylaminophenyl)-p-phenylenediimonium and 3 g of a 20% cyclohexanone solution of a polyester resin (Biron 200; manufactured by Toyobo Co. Ltd.) were mixed and coated by a bar coater on the polyethylene terephthalate resin side on the side opposite to the squarylium compound-containing layer side of the filter prepared in Example 1-1, followed by drying to obtain a coating film having a thickness of 6 μm.

This coating film was measured by Hitachi spectrophotometer (U-3500). The wavelength at the minimum value of the transmittance was 1100 nm.

EXAMPLE 1-10

Example for Forming an Electromagnetic Wave Screening Layer and a Non-glare Layer An ITO thin film was laminated on the diimonium type compound-containing layer side of the filter prepared in Example 1-9 by using an indium oxide/tin oxide sintered body and using an argon gas and an oxygen gas. Further, the side having no non-glare layer formed of a PMMA sheet (acryl filter MR-NG, manufactured by Mitsubishi Rayon Co., Ltd.) having a thickness of 3 mm and having an antiglare layer on the other side, and the ITO side of the above filter were bonded to obtain a filter for a plasma display panel, whereby a good filter was prepared.

EXAMPLE 2-1 AND COMPARATIVE EXAMPLE 2-1

1) 0.36 g of a 0.63% PGMEA (polypropylene glycol-1-monomethylether-2-acetate) solution of a squarylium compound of the formula (I') wherein m=3 (substituted positions: 2, 4 and 6-positions) and 3 g of a 20% PGMEA solution of a polyester resin (Biron 200; manufactured by Toyobo Co. Ltd.) were mixed and coated by a bar coater on a polyethylene terephthalate film (PET film "T100E" manufactured by Diawheelhekist Company, thickness: 100 μm), followed by drying to obtain a coating film having a thickness of 6 μm.

Figure 3:
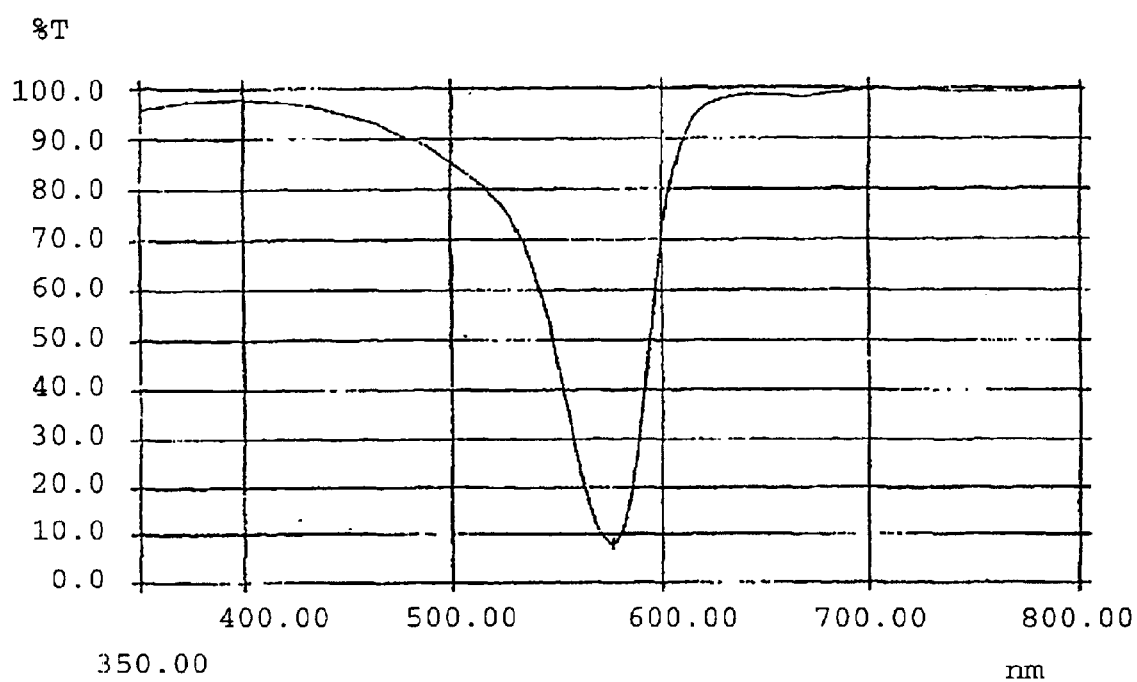
FIG. 3 shows a transmittance curve of the coating film obtained in Example 2-1.

The transmittance of this coating film was measured by Hitachi spectrophotometer (U-3500). The transmittance curve is shown in FIG. 3. The wavelength at the minimum value of the transmittance was 576 nm, and the transmittance was 8.2%. Further, in this case, the wavelength width at a transmittance of 50% was 47 nm, and there was no minimum value in the transmittance curve other than at 576 nm. Further, a neon emission screening filter having a good transmittance having no minimum value in transmittance other than the minimum value at 576 nm, was obtained. Further, the visual light transmittance of this neon emission screening film was 57%, and it was a bright filter having a high transmittance.

2) An ultraviolet absorbing coating fluid containing an isocyanate resin as a binder and zinc oxide as an ultraviolet absorber (ZR-133 (4.9 wt % of a curing agent was added), manufactured by Sumitomo Osaka Cement Co., Ltd.) was coated by a bar coater on the polyethylene terephthalate resin side on the side opposite to the squarylium compound-containing layer side of the coating film of the above 1), followed by drying to form an ultraviolet absorbing layer having a thickness of 3 μm, whereby a filter for a plasma display panel having good light resistance was obtained. The wavelength at the 50% transmittance of this ultraviolet absorbing layer was 383 nm.

Using a xenon fadeometer (FAL-25AX-HC.B.EC, manufactured by Suga Test Instruments Co., Ltd.), evaluation of light resistance was carried out (80-hour exposure) as between a case where the above ultraviolet absorbing layer of a neon emission screening filter was formed (Example 2-1) and a case where no such layer was formed (Comparative Example 2-1). The colorant-remaining ratio (%) was measured by the absorption by Hitachi spectrophotometer (U-3500), whereby it was 98.4% with the former, while it was 83.2% with the latter.

The former was exposed from the ultraviolet absorbing layer side, and the latter was exposed from the squarylium compound-containing layer side.

EXAMPLE 2-2 and COMPARATIVE EXAMPLE 2-2

Example Wherein the Binder Resin was Changed

1) Using a 20% PGMEA solution of an acrylic resin (BR-83; manufactured by Mitsubishi Rayon Co., Ltd.)

instead of the 20% PGMEA solution of the polyester resin (Biron 200; manufactured by Toyobo Co. Ltd.) of Example 2-1, a coating film having a thickness of 6 μm containing the squarylium compound of Example 2-1 in the same concentration as in Example 2-1, was formed on the polyethylene terephthalate film (PET film "T100E" manufactured by Diawheelhekist Company, thickness: 100 μm).

The transmittance of this coating film was measured by Hitachi spectrophotometer (U-3500). The wavelength at the minimum value of the transmittance was 566 nm, and the transmittance was 8.5%.

2) A Sharp Cut Filter SC-38 (manufactured by Fuji Photo Film Co., Ltd.) was laminated on the polyethylene terephthalate resin side on the side opposite to the squarylium compound-containing layer side of the coating film of the above 1), to obtain a filter for a plasma display panel having good light resistance. The wavelength at the 50% transmittance of this ultraviolet absorbing layer was 379 nm.

Using a xenon fadeometer (FAL-25AX-HC.B.EC, manufactured by Suga Test Instruments Co., Ltd.), evaluation of light resistance was carried out (80-hour exposure) as between a case where the ultraviolet absorbing layer of a neon emission screening filter was laminated (Example 2) and a case where no such layer was laminated (Comparative Example 2). The colorant-remaining ratio (%) was measured by the absorption by Hitachi spectrophotometer (U-3500), whereby it was 74.9% with the former, while it was 55.4% with the latter.

The former was exposed from the ultraviolet absorbing layer side, and the latter was exposed from the squarylium compound-containing layer side.

EXAMPLE 2-3 AND COMPARATIVE EXAMPLE 2-3

1) 0.36 g of a 0.63% cyclohexanone solution of 2-(2'-hydroxy-3',5'-di-t-butylphenyl)benzotriazole and 3 g of a 20% cyclohexanone solution of a polyester resin (Biron 200; manufactured by Toyobo Co. Ltd.) were mixed and coated by a bar coater on the polyethylene terephthalate resin side on the side opposite to the squarylium compound-containing layer side of the coating film of Example 2-1, followed by drying to obtain a coating film having a thickness of 6 μm (an ultraviolet absorbing layer-laminated film). The wavelength at the 50% transmittance of this ultraviolet absorbing layer was 390 nm.

2) 0.058 g of 2-(2'-hydroxy-3',5'-di-t-butylphenyl) benzotriazole, 3 g of a 20% cyclohexanone solution of a polyester resin (Biron 200; manufactured by Toyobo Co. Ltd.), and 0.36 g of a 0.63% cyclohexanone solution the squarylium compound as used in Example 2-1, were mixed and dissolved and coated by a bar coater on a PET film "T100E" manufactured by Diawheelhekist Company, followed by drying to obtain a coating film having a thickness of 6 μm (a colorant/ultraviolet absorber mixed film).

Using a xenon fadeometer, evaluation of light resistance was carried out (80-hour exposure) with respect to the above ultraviolet absorbing layer-laminated film (Example 2-3) and the colorant/ultraviolet absorber mixed film (Comparative Example 2-3). The colorant-remaining ratio (%) was measured by the absorption by Hitachi spectrophotometer (U-3500), whereby it was 97.4% with the former, while it was 88.9% with the latter.

The former was exposed from the ultraviolet absorbing layer side.

EXAMPLE 2-4

Example Wherein the Squarylium Compound was Changed 0.36 g of a 0.63% cyclohexanone solution of a squarylium compound of the formula (I') wherein m=2 (substituted positions: 2 and 4-positions) and 3 g of a 20% dimethoxy ethane solution of a polyester resin (Biron 200; manufactured by Toyobo Co. Ltd.) were mixed and coated by a bar coater on a polyethylene terephthalate film (PET film "T100E" manufactured by Diawheelhekist Company, thickness: 100 μm), followed by drying to obtain a coating film having a thickness of 6 μm. The transmittance of this coating film was measured by Hitachi spectrophotometer (U-3500). The wavelength at the minimum value of the transmittance was 599 nm.

In the same manner as in Example 2-1, a zinc oxide-containing ultraviolet absorbing layer having a thickness of 3 μm was formed on the polyethylene terephthalate resin surface on the side opposite to the squarylium compound-containing layer side of this coating film, to obtain a filter for a plasma display panel having good light resistance. The wavelength at the 50% transmittance of this ultraviolet absorbing layer was 383 nm.

EXAMPLE 2-5

Example for Forming a Near Infrared Screening Layer 0.36 g of a 0.63% cyclohexanone solution of a diimonium type near infrared absorbing dye (a hexafluoroantimonate of N,N,N',N'-tetrakis(p-dibutylaminophenyl)-p-phenylenediimonium) and 3 g of a 20% cyclohexanone solution of a polyester resin (Biron 200; manufactured by Toyobo Co. Ltd.) were mixed and coated by a bar coater on the polyethylene terephthalate resin surface on the side opposite to the squarylium compound-containing layer side of the filter prepared in Example 2-1, followed by drying to obtain a coating film having a thickness of 6 μm.

This coating film was measured by Hitachi spectrophotometer (U-3500). The wavelength at the minimum value of the transmittance was 1100 nm.

EXAMPLE 2-6

Example for Forming an Electromagnetic Screening Layer and a Non-glare Layer An ITO thin film was laminated on the diimonium type compound-containing layer side of the filter prepared in Example 2-5 using indium oxide/tin oxide sintered body and using an argon gas and an oxygen gas. Further, the ITO side of the above filter was bonded to the side having no non-glare layer formed, of a PMMA sheet (acryl filter MR-NG, manufactured by Mitsubishi Rayon Co., Ltd.) having a thickness of 3 mm and having an antiglare layer on the other side, to obtain a film for a plasma display panel, whereby a good filter was obtained.

INDUSTRIAL APPLICABILITY

The filter for a plasma display panel having a layer containing the squarylium compound represented by the formula (I), of the present invention, is excellent in the neon emission screening performance, the near infrared shielding performance, the visible light transmitting performance, the electromagnetic screening performance, the antireflection performance, the glare-preventing performance and the light resistance.

The entire disclosures of Japanese Patent Application No. 11-57944 filed on Mar. 5, 1999, Japanese Patent Application No. 11-296832 filed on Oct. 19, 1999 and Japanese Patent Application No. 11-306563 filed on Oct. 28, 1999 including specifications, claims, drawings and summaries are incorporated herein by reference in their entireties.

What is claimed is:

1. A squarylium compound having the formula (I):

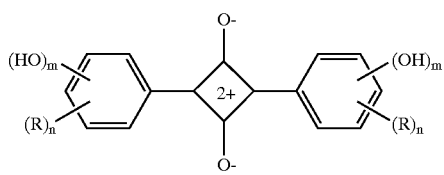
(I)

wherein R is $C_{1-20}$ linear or branched alkoxy which is optionally substituted; m is an integer of from 1 to 4; and n is an integer of from 1 to 4.

2. The squarylium compound of claim 1, wherein R is $C_{1-6}$ alkoxy.

3. A squarylium compound having formula (I):

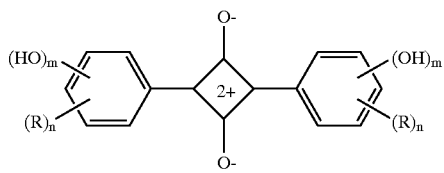
(I)

wherein m is 3, n is 1 and R is alkyl which is optionally substituted.

4. The squarylium compound of claim 3, wherein R is —CH$_3$.

5. The squarylium compound of claim 3, wherein R is n-C$_3$H$_7$.

6. A squarylium compound having the formula (I):

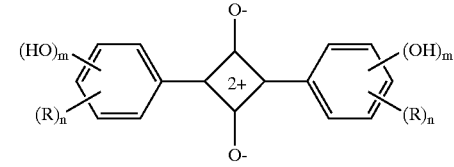

Wherein m is 2, n is 1, and R is —OCH$_3$ or n-OC$_4$H$_9$.

7. The squarylium compound of claim 3, having an absorption maximum in a range of about 580 to 600 nm.

8. The squarylium compound of claim 3, wherein R is —C$_5$H$_{11}$, -n-C$_4$H$_9$, —CH$_2$C(CH$_3$)$_3$, —CH$_2$C$_6$H$_5$, or —CH$_2$CH(C$_2$H$_5$)C$_5$H$_{11}$.

9. A filter for a plasma display panel, comprising a layer containing an ultraviolet absorber laminated on a layer containing one or more squarylium compounds of the formula (I'):

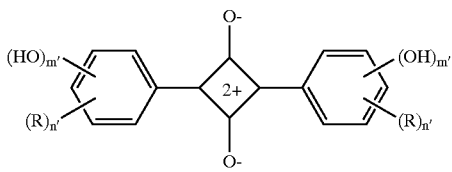
(I')

wherein:
R is halogen, alkyl which is optionally substituted, alkoxy which is optionally substituted, or alkenyl which is optionally substituted; m' is an integer of from 1 to 4; and n' is an integer of from 0 to 4.

10. The filter for a plasma display panel of claim 9, wherein for at least one of the squarylium compounds n'=0.

11. The filter for a plasma display panel of claim 9, wherein for at least one of the squarylium compounds n'=0, and m'=2 or 3.

12. The filter for a plasma display panel of claim 9, wherein R is an alkyl group which is optionally substituted.

13. The filter for a plasma display panel of claim 9, wherein m'=3, and n'=1.

14. The filter for a plasma display panel of claim 9, having a visible light transmittance is at least 40%.

15. The filter for a plasma display panel of claim 9, which further comprises a near infrared screening layer.

16. The filter for a plasma display panel of claim 9, which further comprises an electromagnetic wave screening layer.

17. The filter for a plasma display panel of claim 9, which further comprises an antireflection layer.

18. A filter for a plasma display panel, comprising a layer which contains one or more squarylium compounds having the formula (I):

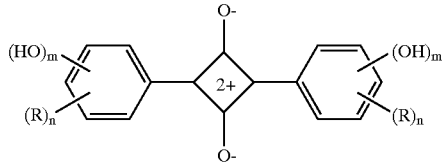

wherein:
R is halogen, alkyl which is optionally substituted, alkoxy which is optionally substituted, or alkenyl which is optionally substituted; m is an integer of from 1 to 4; and n is an integer of from 1 to 4 and which further comprises a glare-preventing (non-glare) layer.

19. A plasma display panel device, comprising the filter for a plasma display panel of claim 9, on a screen of a plasma display panel.

20. The filter for a plasma display panel of claim 9, comprising a UV ray-absorbing layer on a light irradiation side of the filter.

* * * * *